United States Patent
Wohltjen

(10) Patent No.: US 7,240,535 B2
(45) Date of Patent: Jul. 10, 2007

(54) METHOD AND APPARATUS FOR GAS MEASUREMENT AT SUBSTANTIALLY CONSTANT PRESSURE

(75) Inventor: Henry Wohltjen, Bowling Green, KY (US)

(73) Assignee: Microsensor Systems, Inc., Bowling Green, KY (US)

( * ) Notice: Subject to any disclaimer, the term of this patent is extended or adjusted under 35 U.S.C. 154(b) by 0 days.

(21) Appl. No.: 11/221,208

(22) Filed: Sep. 7, 2005

(65) Prior Publication Data
US 2007/0051163 A1 Mar. 8, 2007

(51) Int. Cl.
*G01N 30/04* (2006.01)
(52) U.S. Cl. .................................... 73/23.42
(58) Field of Classification Search .............. 73/23.42; 250/345
See application file for complete search history.

(56) References Cited

U.S. PATENT DOCUMENTS

| | | | |
|---|---|---|---|
| 4,019,863 A | 4/1977 | Jenkins et al. | |
| 4,177,677 A | 12/1979 | Ruzicka et al. | |
| 4,316,382 A | 2/1982 | Woodruff | |
| 4,388,411 A | 6/1983 | Lovelock | |
| RE31,438 E | 11/1983 | Ueda | |
| 4,565,086 A * | 1/1986 | Orr, Jr. | 73/19.09 |
| 4,902,896 A | 2/1990 | Fertig et al. | |
| 5,187,972 A * | 2/1993 | DeFriez | 73/23.2 |
| 5,332,901 A | 7/1994 | Eckles et al. | |
| 5,340,987 A | 8/1994 | Eckles et al. | |
| 5,342,580 A * | 8/1994 | Brenner | 422/92 |
| 5,457,320 A * | 10/1995 | Eckles et al. | 250/345 |
| 6,244,096 B1 * | 6/2001 | Lewis et al. | 73/23.2 |
| 6,397,660 B1 | 6/2002 | Kikuchi et al. | |
| 6,467,333 B2 * | 10/2002 | Lewis et al. | 73/31.05 |
| 6,550,308 B2 | 4/2003 | Kikuchi et al. | |
| 6,649,129 B1 * | 11/2003 | Neal | 422/89 |
| 6,841,391 B2 * | 1/2005 | Lewis et al. | 436/149 |
| 2002/0017125 A1 * | 2/2002 | Lewis et al. | 73/31.05 |
| 2003/0136176 A1 | 7/2003 | Ruiz | |

* cited by examiner

*Primary Examiner*—Hezron Williams
*Assistant Examiner*—John Fitzgerald
(74) *Attorney, Agent, or Firm*—Kramer Levin Naftalis & Frankel LLP

(57) ABSTRACT

A system which enables the presentation of alternating gas samples to a gas sensor in a detection zone without substantial change of the sample pressure at the sensor in the zone, whereby pressure variations that can produce unwanted sensor signals are mitigated; along with apparatus for facilitating, and a method for implementing, the foregoing.

27 Claims, 2 Drawing Sheets

METHOD AND APPARATUS FOR GAS MEASUREMENT AT SUBSTANTIALLY CONSTANT PRESSURE

FIELD OF THE INVENTION

The present invention relates to the detection of a gas species in a gas sample. More specifically, this invention relates to a system, apparatus and methods for detection of a gas species in a gas sample wherein inaccuracies introduced by noise or drift stemming are mitigated.

BACKGROUND OF THE INVENTION

The sensing of gases is important to many endeavors such as environmental monitoring, patient care, anesthesiology, personal safety, and process control. The electronic gas sensors typically used in these applications feature transduction mechanisms that rely on surface interaction (e.g., absorption or adsorption) of an analyte gas. The amount of interaction, and hence the output signal from these sensors, generally is proportional to the partial pressure of the analyte gas in the gas sample contacted with the sensor.

More specifically, gas sensors are susceptible to noise that can affect the signal from the sensor. One type of drift noise, also called "flicker noise," is characterized by slowly varying signals resulting from temperature variations and/or "aging" of the sensor.

Drift noise resulting from "aging" of the sensor often exhibits a magnitude that is. inversely proportional to the frequency at which "zero" measurement signals are taken using the sensor. In other words, drift noise $\approx 1/f$, where f is the frequency. As frequency is inversely proportional to the time between "zero" measurements (i.e., $f=1/t$, where t is the time), drift noise will be proportional to the time between zero measurements (i.e., drift noise $\approx 1/(1/t)$ t). Where the measurement of gas concentrations is accomplished over a period of hours or days, the result will be very large measurement periods (t), very small frequency values (f), and correspondingly high values of 1/f. In summary, the longer the interval between zero adjustments of the sensor, the greater the amount of drift that is likely to be observed.

Conducting a "zero" measurement immediately followed by a "target" measurement could minimize drift by minimizing the interval between zero adjustments. But such approach has not been effective, because it creates another source of drift or noise when a pump is utilized to effect gas-flow to the sensor—i.e., pressure variation in the measurement zone at the sensor element. This can be seen from a more detailed analysis of the mechanisms at work. Thus, to secure a reference measurement an analyte gas and/or unwanted contaminants are, for example, removed by a trap (often referred to as a "scrubber") through the use of physical and/or chemical means. A "zero" measurement is provided by exposing the sensor to the gas sample from the trap. Thereafter, a "target" (or normal) measurement is taken by exposing the sensor to a gas sample not previously contacted with the trap. Ideally, the subtraction of the "zero" measurement from the "target" measurement provides a signal that has not been corrupted by long-term drift, especially where the period between the "zero" and "target" measurements can be kept short. Systems designed to reduce the effects of sensor baseline drift "noise" on the measurement typically have a valve located before the sensor, allowing switching of the flow to the sensor between a trap (which provides the "zero" reference gas sample to the sensor) and a direct source providing the "target" gas sample. However, flow switching of this sort tends to result in pressure changes in the measurement zone at the sensor which themselves cause noise that detracts from the sensitivity and accuracy of detection.

In connection with the foregoing, a number of known fluid analysis systems utilize means for switching between two or more fluid sources. For example, the infrared gas analyzing apparatus of U.S. Pat. No. RE31,438 discloses a valve system connected to two analysis cells, wherein the flow from two sources can be alternated between the analysis cells. The infrared fluid analyzer of U.S. Pat. No. 4,902,896 (Fertig et al.) uses a single valve switch for alternating flow to the pump between a raw fluid source and a "calibration" fluid source. The gas analyzing apparatus of U.S. Pat. Nos. 5,332,901, 5,340,987, and 5,457,320 (Eckles et al.) features a gas valve for the provision of either a processed or unprocessed gas to the apparatus' infrared sensor. U.S. Pat. Nos. 6,397,660 and 6,550,308 (Kikuchi et al.) disclose a gas analyzing apparatus with a valve system for switching between an unprocessed gas sample and processed gas sample.

More specifically, while periodically shifting between a "zero" gas sample and "target" gas sample is effective in reducing drift noise due to temperature change or "aging," conventional systems experience problems with sensor noise due to the pressure variations caused when the flow to the sensor is modulated from the "zero" reference source to the "target" source. Unfortunately, any variation in pressure at the gas sensor will result in a corresponding variation in the sensor signal. Thus, pressure variation will introduce an independent source of "noise" to the sensor signal output.

Some gas sensors rely on passive diffusion to bring the analyte gas to the sensor. In this case, the pressure of the total gas sample is the same as the ambient atmospheric pressure. Atmospheric pressure variations are limited in magnitude and usually occur slowly. It follows that sensors using passive gas sampling are not normally afflicted with serious problems of sample pressure induced variation in sensor output signals. But, for certain important applications this is not a real world answer, as most high performance gas detection and measurement systems require a sampling pump to bring known quantities of representative gas samples to the sensing element quickly. Pumps generate a significant pressure differential to cause gas flow, and abrupt switching from one pressurized gas stream to another can cause a pressure variation. If the gas pressure at the sensor varies then the sensor signal will vary. Pump pressure variations, therefore, introduce a source of noise to the sensor signal output. Even though ordinarily for high precision gas sensing, the pumps utilized cause no more than modest pressure variation, this still introduces a disadvantageous amount of additional noise. And, of course, the high performance of more substantial pumps is sacrificed.

In any event, the problem with pressure variations is much more pronounced in systems where it is desired to use a valve ahead of the sensor to switch the sensor flow between a scrubber trap (to provide a "zero" reference gas to the sensor by removing unwanted contaminants from the gas sample) and the direct source of the gas sample. A typical system of this sort is illustrated in FIG. 1. The purpose of such a system is to reduce the effects of sensor baseline drift "noise" on the measurement.

A strategy to remedy this problem is to match the flow restriction imposed by the direct flow path to that of the trap. While this strategy may offer some improvement, it still is not adequately effective because the pressure of the gas present at the connection between the trap and the valve (or, alternately, between the direct sample path and the valve) changes drastically whenever the valve is switched to the other path and the flow to the pump vacuum is interrupted. This change in pressure at the measurement situs introduces "noise" and/or other inaccuracy.

The development of a simple method and apparatus for analyzing gas samples, which minimize the effects of noise and drift, by decreasing the interval between "zero" and target measurements and also providing the ability to alternate the flow to the sensor between a reference gas source and target gas source while maintaining a substantially constant pressure at the sensor, would be a significant step forward in the art.

OBJECTS OF THE INVENTION

It is an object of the invention to provide a system, apparatus and method to modulate the presentation of a gas sample to a sensor while maintaining a substantially constant sample pressure at the sensor.

It is another object of the invention to provide a system, apparatus and method suitable for the rapid, accurate, and reliable detection of a selected gas species in a gas sample.

It is yet another object of the invention to provide system, apparatus and methods suitable for enhancing the selectivity of the detection of analyte gas species.

It is a further object of the invention to provide a system, apparatus and method that facilitate making pairs of zero/target measurements having a minimized interval between the pair of measurements without concomitant noise resulting from pressure changes at the measurement site flowing from the manner in which the interval between paired measurements is minimized.

The foregoing and other additional objects of the invention are met by the invention as follows.

SUMMARY OF THE INVENTION

The focus of this invention is to achieve the presentation of alternating gas samples to a gas sensor in a detection zone without substantial change of the sample pressure at the sensor or in the zone. The invention is directed to mitigation (e.g., reduction or substantial elimination) of pressure variations that can produce unwanted sensor signals. (For purposes of this disclosure, and throughout the same, the term "mitigate" and any derivative or variation thereof shall mean or refer to causing to become less harsh, severe or otherwise adverse.) In the case of gas mixtures, the invention also provides a way of conducting differential measurements with reduced measurement noise and drift and increased selectivity. The substantially constant pressure of the sample in the detection zone, at the sensor, combined with rapid differential measurements, permits the quick detection of trace level concentrations of specific gases in complex atmospheres. (For purposes of this disclosure, and throughout the same, the term "measure" and any derivative or variation thereof shall mean and encompass a qualitative as well as a quantitative determination (i.e., detection as well as numerical characterization)).

Accordingly, in one aspect the invention is a system for normalized detection of gas emanating from a fluid source, which comprises: a sensor for detection of a select gas species; a trap for said gas species or for one or more unwanted gas species; a pump for inducing gas-flow in said system; a plurality of valve assemblies, each said valve assembly being interconnected with said sensor; said plurality of valve assemblies including a first valve assembly also interconnected with said trap, which trap is interconnected with said fluid source, said first valve assembly being variable between a first position in which it affords a path between the sensor and the trap and a second position in which it affords a path between the trap and the pump circumventing the sensor; and said plurality of valve assemblies including a second valve assembly also interconnected with said fluid source, said second valve assembly being variable between a first position in which it affords a path between the sensor and said fluid source and a second position in which it affords a path between the pump and said fluid source circumventing the sensor.

In a further aspect, the invention is an apparatus for dispensing alternating fluid feeds in gas form from a fluid source to a detection sensor under the action of a pump to induce the flow of such feeds to the sensor, comprising: a trap for a select gas species or for one or more unwanted gas species; a plurality of valve assemblies, each said valve assembly being adapted for interconnection with said detection sensor and with said pump; said plurality of valve assemblies including a first valve assembly interconnected with said trap, which trap is adapted for interconnection with said fluid source, said first valve assembly being variable between a first position in which it affords a path between the trap and said sensor when interconnected therewith and a second position in which it affords a path between said trap and said pump when interconnected therewith which latter path circumvents the sensor; and said plurality of valve assemblies including a second valve assembly adapted for interconnection with said fluid source, said second valve assembly being variable between a first position in which it affords a path between the sensor and said fluid source when interconnected therewith and a second position in which it affords a path between the pump and said fluid source when interconnected therewith, which latter path circumvents the sensor.

In another aspect, the invention is a method of dispensing alternating fluid feeds in gas form from a fluid source to a detection sensor, which comprises: inducing fluid in gas form to flow alternately (a) from said fluid source along a first path through a trap for a select gas species that may be present in said fluid in gas form, or for one or more unwanted gas species, such that the throughput from the trap comes in contact with said detection sensor, and (b) from said fluid source along a second path circumventing the trap such that said fluid in gas form comes in contact with said detection sensor; operating a plurality of valve assemblies located variously along said first and second paths such that alternately (i) the throughput of said trap is fed to said detection sensor from said first path while the flow from said second path is diverted around said sensor, and (ii) the flow from said second path is fed to said detection sensor while the throughput of said trap from said first path is diverted around said sensor, whereby the pressure at the detection sensor remains substantially constant; said plurality of valve assemblies including a first valve assembly interposed along said first path between the trap and the detection sensor, said first valve assembly being variable between a first position in which it affords a path from the trap to the sensor and a second position in which it affords a path that diverts flow from the trap around the sensor; and said plurality of valve assemblies including a second valve assembly interposed along said second path between the fluid source and the detection sensor, said second valve assembly being variable between a first position in which it affords a path from the fluid source to the sensor and a second position in which it affords a path that diverts flow from said fluid source around the detection sensor.

The invention confers significant advantages on its practitioner. It permits faster detection of gases, at lower limits of detection, with improved selectivity, and represents a substantial improvement over the conventional art. The invention enables performance of a zero/target measurement couplet with a minimal interval between the measurements by countering pressure variations intrinsic to the otherwise ideal approach for the performance of small interval measurements, and thus mitigates undesirable divergences in the sensor signal that would occur if such counter-measure were not incorporated as part of the invention. That is, the invention enables quick differential measurements without introducing other noise and drift causes that undercut the efficacy of small-interval measurements in the first place. The unique ability of the invention to maintain a constant pressure at the gas sensor, combined with the aforementioned rapid differential measurement, permits the quick detection of trace level concentrations of specific gases in complex atmospheres.

DESCRIPTION OF CERTAIN PREFERRED EMBODIMENTS

Figure 1:
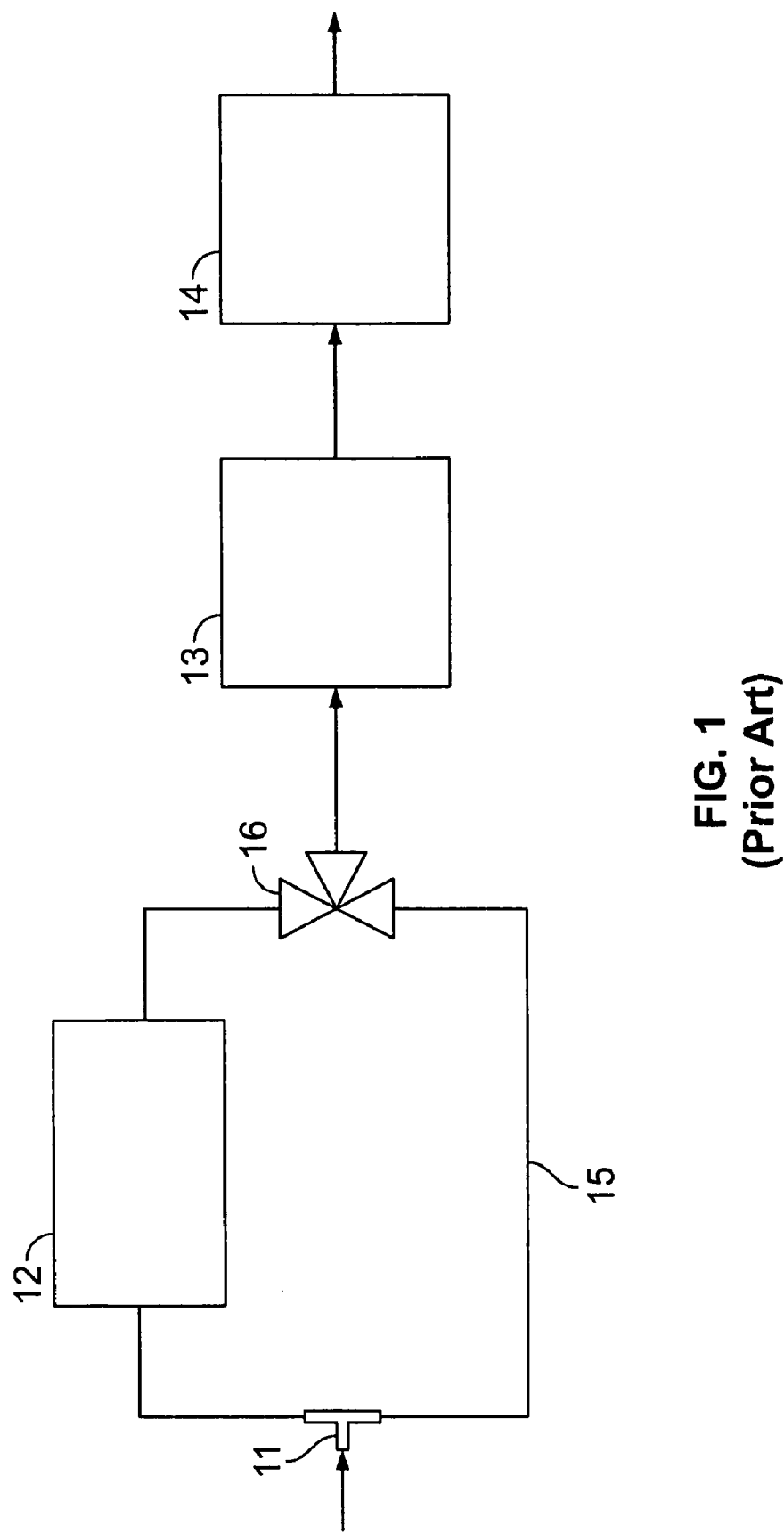
FIG. 1 is a schematic diagram showing a conventional gas measurement apparatus.

This invention provides a system, apparatus and method as aforesaid that can permit faster detection of gases, at lower limits of detection, and with improved selectivity. It is applicable to all gas sensors but it is particularly useful for surface sorption based sensors.

As indicated above, the essence of the present invention is analysis of a gas sample utilizing a combined rapid-differential-measurement/constant-pressure-maintenance approach. The gas sample can consist of any fluid sample in the gaseous phase (e.g., ambient air, human breath, or a process stream). By means of this innovative approach noise/drift which would otherwise make the implementation of rapid differential measurement unavailing is mitigated in a manner that does not counterproductively substitute a different source of noise/drift for the one originally targeted.

Accordingly, a central feature of the present invention is the deployment of rapid differential measurement technology in tandem with maintenance of a constant pressure in the zone of detection by a gas sensor. This is accomplished by delivery of gas samples to a sensor in the zone of detection in alternating fashion, at least in part along flowpaths arranged in parallel (functionally speaking), one of which flowpaths incorporates a trap for (inter alia) the gas species to be detected or for one or more unwanted gas species and the other of which is effectively unobstructed, and concomitantly keeping the gas pressure at the gas sensor in the zone of detection substantially unchanged. To that end, rather than flowpaths arranged in parallel which feed to a valve assembly that simply shuts off one flowpath so that it no longer communicates with the detection zone and sensor therein, while opening the other flowpath so it can communicate with the zone/sensor, the invention is in the utilization of at least two valve assemblies. According to the invention, one of the flowpaths feeds to one of the valve assemblies and the other of the flowpaths feeds to a second one of the valve assemblies, each of the valve assemblies alternately permitting communication of the flowpath feeding to it with either the detection zone and sensor therein or a shunt line that circumvents the zone/sensor and is interconnected with the pump. The valve assemblies are actuated such that when one is in position to allow communication between its corresponding flowpath and the zone/sensor the other is in position to shut off communication of its corresponding flowpath with the zone/sensor and instead allow that flowpath to communicate with the shunt line as aforesaid. By causing each flowpath to be continually subject to the influence of the pump, whether the flowpath is in communication with the detection zone/sensor or a shunt line, a substantially constant gas flow and pressure are maintained in the measurement zone and/or at the sensor. The removal of the pressure differential due to flowpath alternation results in the reduction of a major source of sensor noise and/or other inaccuracy and allows for dramatically improved limits of detection.

The sensors of the invention are components that emit a change in output signal when exposed to a selected gas analyte in the gas sample. The sensor of the invention can be chosen from a broad spectrum of gas sensor technologies compatible with practice of the invention and the particular application of interest, including without limitation metal oxide semiconductors (MOS), amperometric and voltametric electrochemical cells, coated bulk acoustic wave (BAW) resonators, coated surface acoustic wave (SAW) resonators, pellistors, thermal conductivity detectors, conductive polymers, chemiresistors, photoionization detectors, chemically sensitive field effect transistors, and optical waveguide sensors. The transduction mechanism of the sensor technologies cited herein depends on the sorption of the analyte gas to be detected by either a polymer, membrane, electrolyte, or MOS surface. While the invention can be practiced using all gas sensors, it is particularly useful for surface sorption based sensors.

A conventional apparatus wherein a valve is used to modulate the flow to the gas sensor between two different gas streams, but wherein such modulation leads to undesirable pressure changes as discussed above, is shown in the schematic diagram of FIG. 1. A pump 14 creates a significant pressure differential causing the "sample" gas to enter at the inlet 11. Upon entering the inlet 11, the "sample" gas, will flow either through the trap 12 or through the direct flow path 15, depending on the position of the valve 16. In the first position of the valve 16, the sample gas will pass through the trap 12 and to the sensor 13 while flow through direct flow path 15 is blocked; in the second position, the sample gas will pass through the direct flow path 15 and to the sensor 13 while flow from trap 12 to sensor 13 is blocked. By varying the position of the valve 16, the gas source presented to the sensor 13 can be modulated between a gas source that has passed through the trap 12—the "zero" sample—and a gas source that has passed through the direct flow path—the "target" sample. However, this has the disadvantages discussed in preceding paragraphs because there is no measure implemented to mitigate pressure changes in the detection zone at the sensor.

Figure 2:
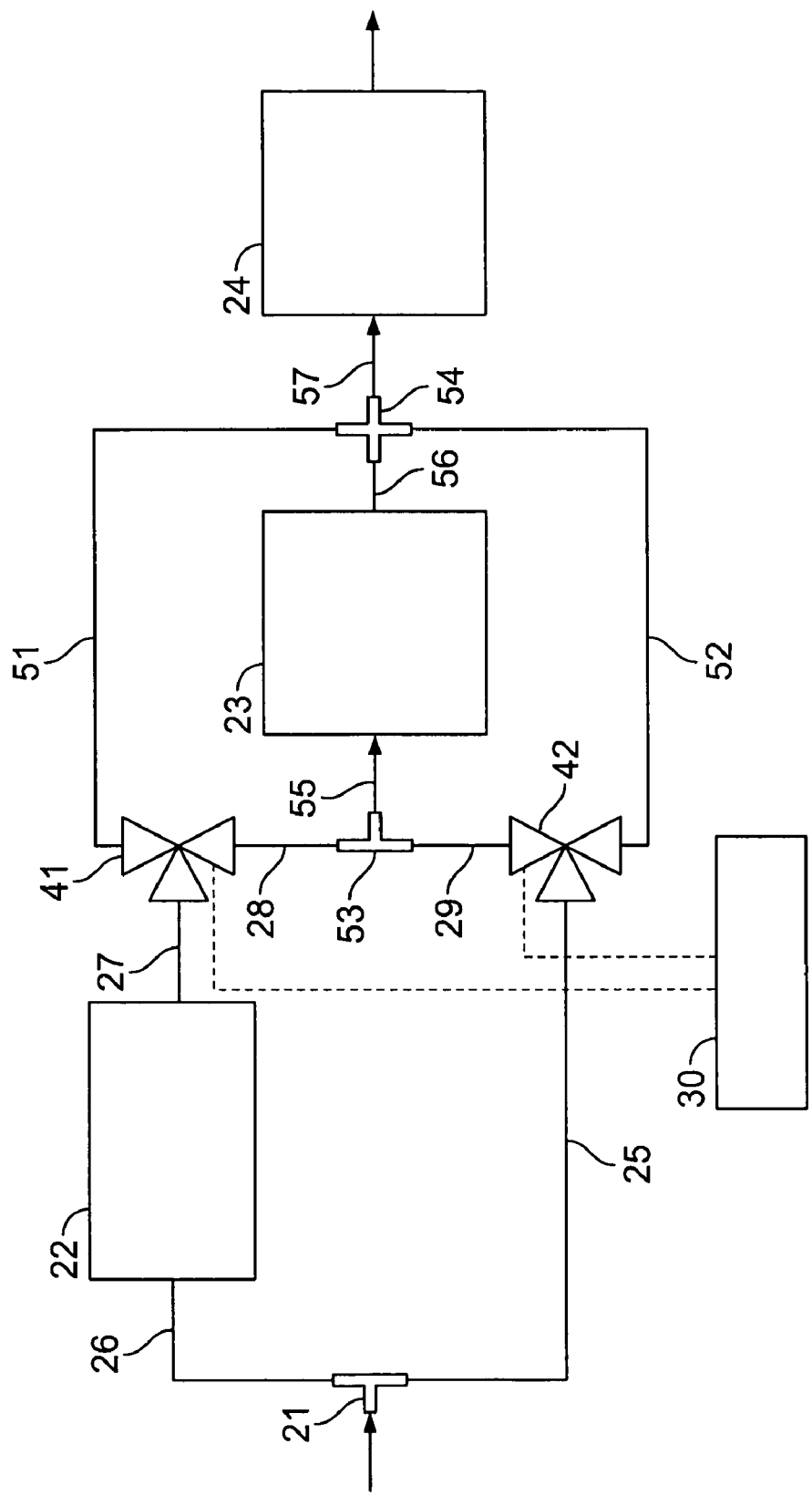
FIG. 2 is a schematic diagram showing an embodiment of a gas measurement apparatus according to the present invention.

In contrast, various features and advantages of the invention can be further understood with respect to FIG. 2. The gas sample is drawn through the inlet 21 of the gas measurement apparatus via a pump 24. Any suitably sized and powered pump capable of drawing the sample into the apparatus can be used.

Once the sample enters the inlet 21, a portion of the sample will flow through line 26, and then trap 22 and line 27 to valve 41 and the remainder of the sample through line 25 to valve 42. Line 25 is effectively unobstructed. Trap 22 (sometimes referred to as a "scrubber") either physically (e.g., via cryogenic temperature), or chemically (e.g., via chemical sorbents, such as activated charcoal or Tenax™, or chemically reactive media), or a combination of the foregoing prevents on a selective basis an analyte gas (or alternatively one or more unwanted gas species) from passing through the trap. Thus, any change in signal due to drift can be eliminated as well as any flow/pressure-change related noise or measurement inaccuracies.

Typically, one trap is sufficient, but in several other good embodiments of the invention a multiplicity of traps with different sorbent materials are utilized; of course, when there is more than one trap, a multiplicity of sensors having varying chemical selectivities is advantageously utilized as well so that a spectrum of gas species in a sample can be analyzed.

The flowpaths of the respective gas streams after reaching valve 41 and valve 42 will be determined by the respective positions of those valves. In its first position, valve 41 permits the flow of the gas from the trap 22 and line 27 into line 28, through junction 53 and line 55 to sensor 23; in its second position, valve 41 permits the flow of the gas from trap 22 and line 27 into shunt line 51, through junction 54 and line 57 to pump 24, thus circumventing the sensor. Similarly, in its first position, valve 42 permits the flow of the gas from line 25 into line 29, through junction 53 and line 55, to sensor 23; in its second position, valve 42 permits the flow of the gas from line 25 into shunt line 52, through junction 54 and line 57 to pump 24, thus circumventing the sensor. Any material compatible with the gaseous fluid to be measured, and strong enough to withstand the relevant pressures, can be used for the structure defining the gas flow paths and pressure-tight sensor cell. Generally, materials that are non-porous and non-sorptive of the gases, for instance, stainless steel, nickel or non-porous inert plastics (e.g., teflon derivatives such as PFA teflon), are preferred.

The operation of valves 41 and 42 is regulated by a processor 30, which directs (among other things typically) the relative positions of the valves to effect proper flow to the sensor. The processor 30 can consist of a computer microcontroller or any other device capable of directing the operation of the valves. Valves 41 and 42 can be any type of suitable conventional assembly, for instance, components which are electrically powered or air powered.

In a first configuration, valve 41 is in its first position and valve 42 is in its second position. In this configuration, the gas throughput from trap 22 and line 27 will flow into line 28 to sensor 23, while flow from line 25 will enter the shunt line 52 thus bypassing the sensor. In a second configuration, valve 41 is in its second position and valve 42 is in its first position. In this configuration, the gas from line 25 will flow to sensor 23, while flow from trap 22 and line 27 will enter the shunt line 51 thus bypassing the sensor. By modulating between the first and second configuration, the flow to the sensor can be varied between a gas that has been "scrubbed" by the trap, thereby removing selectively an analyte gas or unwanted gas species, and a gas sample that has not passed through the trap.

An advantage the present invention presents over conventional technology is the mitigation of pressure variations in the gas sample presented to the sensor. By providing shunt lines 51 and 52, a constant gas flow and pressure are maintained through trap 22 (along with associated line 27) and line 25, regardless of whether the valves are in the aforementioned first configuration or second configuration.

Further, in several good embodiments of the invention the operation of valves 41 and 42 can be controlled to effect substantial elimination of the pressure changes that occur with conventional devices when the gas flow to the sensor is switched from one source to another. In the FIG. 2 embodiment, because the flow through trap 22 and line 27, as well as the flow through line 25, are both subject to the action of the pump at all times, the flow in each of those lines is never disrupted and consequently is not subject to the abrupt pressure variation which can afflict conventional technology. Processor 30 can be used to cause each valve to switch from its first position to the second position, or vice versa, such that the rate and pressure of the flow to the sensor is held substantially constant.

Accordingly, in a preferred mode of operation of the system, processor 30 will cause valve 41 to change from its first position to its second position at substantially the same time as the processor causes valve 42 to change from its second position to its first position, thus maintaining a constant flow rate to and pressure at sensor 23. At a later time, processor 30 will cause valve 41 to change from its second position to its first position at substantially the same time as the processor causes valve 42 to change from its first position to its second position. By repeating these steps, the flow to the sensor can be alternated between that from trap 22 and that from line 25, thus allowing successive "zero" and "target" measurements. By continually measuring the difference between a "zero" signal and a "target" signal obtained shortly thereafter in the above-described manner, the time difference between the measurement of the "zero" and "target" signals can be held to an insignificant level compared to the time required for the output signal of the sensor to be affected by drift—and yet the "noise" and/or other inaccuracy which could otherwise be introduced due to flow and/or pressure change when the respective gas flows are alternated is mitigated.

In accordance with the foregoing, several preferred embodiments of the invention as follows afford an advantageous technology for determining a gas species in a sample.

A preferred embodiment of the system for normalized gas detection comprises: a sensor for detection of a select gas species; a pump interconnected with said sensor for inducing flow of a gas stream to said sensor; an inlet for a fluid in gas form; a trap for said gas species interconnected with and interposed between said sensor and said inlet, said trap being adapted for flow therethrough of said fluid in order to remove said gas species which may be present; a first valve interposed between said trap and said sensor, said first valve being configured such that in a first position it permits flow of the gas throughput from said trap to said sensor and in a second position it diverts flow of the gas throughput from said trap into a first shunt line circumventing said sensor and interconnected with said pump; an alternative line interconnected with said inlet and said sensor and including a second valve, said second valve being configured such that in a first position it permits flow of the fluid from said inlet to said sensor and in a second position it diverts the flow of the gas fluid from said inlet into a second shunt line circumventing said sensor and interconnected with said pump; and a processor which causes said first valve to be in said first position and said second valve to be in said second position substantially contemporaneously, and causes said first valve to be in said second position and said second valve to be in said first position substantially contemporaneously.

A preferred embodiment of the apparatus for dispensing alternating fluid feeds in gas form at substantially constant pressure to a detection sensor comprises: an inlet for said fluid in gas form; a trap for a select gas species that may be present, said trap being interconnected with said inlet, and said trap also being adapted for flow therethough of said fluid in gas form in order to remove said gas species when present; a first valve in communicating relationship with said trap and adapted for interconnection with said detection sensor, such that when the valve is interconnected with the sensor the valve is between the trap and the sensor, said first valve also being configured such that, when interconnected with the sensor, in a first position it permits flow of the gas throughput of said trap to said detection sensor and in a second position it diverts flow of said gas throughput to a first shunt line circumventing said detection sensor; an alternative line interconnected with said inlet, and in communicating relationship with a second valve adapted for interconnection with said detection sensor and configured such that, when the valve is interconnected with the sensor, in a first position it permits flow of said fluid from said inlet to said detection sensor and in a second position it diverts flow of said fluid into a second shunt line circumventing said sensor; and a processor which causes said first valve to be in said first position and said second valve to be in said second position substantially contemporaneously, and causes said first valve to be in said second position and said second valve to be in said first position substantially contemporaneously.

A preferred embodiment of the method of dispensing alternating fluid feeds in gas form at substantially constant pressure to a detection sensor comprises: inducing fluid in gas form to enter an inlet interconnected (a) with a trap for a gas species that may be present in said fluid in gas form, said trap in turn being interconnected with said detection sensor, and (b) with an alternative line also interconnected with said detection sensor, and causing said fluid in gas form to flow through said trap, and the gas throughput from said trap to flow to said detection sensor, while substantially contemporaneously causing said fluid also to flow through the alternative line and into a shunt line which circumvents the detection sensor, and thereafter causing said fluid in gas form to flow through said alternative line and to said detection sensor while substantially contemporaneously causing said fluid also to flow through the trap, and the gas throughput from said trap to flow into another shunt line which circumvents the detection sensor.

While the foregoing disclosure describes the invention as appropriate, it will be appreciated that numerous modifications and variations (including equivalents) may be devised by those of ordinary skill in the art once in possession of the teachings herein. It is intended that the claims be deemed to encompass all such modifications and variations (including equivalents) as fall within the true spirit and scope of the present invention.

What is claimed is:

1. A system for normalized detection of gas emanating from a fluid source, which comprises:
    a sensor for detection of a select gas species;
    a trap for said gas species or for one or more unwanted gas species;
    a pump for inducing gas-flow in said system;
    a plurality of valve assemblies, each said valve assembly being interconnected with said sensor;
    said plurality of valve assemblies including a first valve assembly also interconnected with said trap, which trap is interconnected with said fluid source, said first valve assembly being variable between a first position in which it affords a path between the sensor and the trap and a second position in which it affords a path between the trap and the pump circumventing the sensor; and
    said plurality of valve assemblies including a second valve assembly also interconnected with said fluid source, said second valve assembly being variable between a first position in which it affords a path between the sensor and said fluid source and a second position in which it affords a path between the pump and said fluid source circumventing the sensor.

2. The system as defined in claim 1, wherein a constant pressure differential prevails across the flow path through the first valve assembly and across the flowpath through the second valve assembly.

3. The system as defined in claim 1, wherein said trap is one in which a physical mechanism is responsible for removal of said gaseous species which may be present.

4. The system as defined in claim 1, wherein said trap is one in which a chemical mechanism is responsible for removal of said gaseous species which may be present.

5. The system as defined in claim 1, wherein said trap is one in which a combination of physical and chemical mechanisms is responsible for removal of said gaseous species which may be present.

6. The system as defined in claim 1, wherein each sensor is selected from the group consisting of metal oxide semiconductors, amperometric electrochemical cells, voltametric electrochemical cells, coated bulk acoustic wave resonators, coated surface acoustic wave resonators, pellistors, thermal conductivity detectors, conductive polymers, chemiresistors, photoionization detectors, chemically sensitive field effect transistors, and optical waveguide sensors.

7. The system as defined in claim 1, further comprising a second trap for a second selected gaseous species interconnected with and interposed between said sensor and said fluid source, said second trap being adapted for flow therethough of said fluid in order to remove said second gaseous species which may be present therein.

8. The system as defined in claim 1, further comprising a second sensor for detection of a second selected gaseous species.

9. A system as defined in claim 1, which further comprises a processor that causes said first valve assembly to be in said first position and said second valve assembly to be in said second position contemporaneously, and causes said first valve assembly to be in second position and said second valve assembly to be in said first position contemporaneously.

10. A system for normalized gas detection, which comprises:
    a sensor for detection of a select gas species;
    a pump interconnected with said sensor for inducing flow of a gas stream to said sensor;
    an inlet for a fluid in gas form;
    a trap for said gaseous species interconnected with and interposed between said sensor and said inlet, said trap being adapted for flow therethough of said fluid in order to remove said gas species which may be present;
    a first valve interposed between said trap and said sensor, said first valve being configured such that in a first position it permits flow of the gas throughput from said trap to said sensor and in a second position it diverts flow of the gas throughput from said trap into a first shunt line circumventing said sensor and interconnected with said pump; an alternative line interconnected with said inlet and said sensor and including a second valve, said second valve being configured such that in a first position it permits flow of the fluid from said inlet to said sensor and in a second position it diverts the flow of the gas fluid from said inlet into a second shunt line circumventing said sensor and interconnected with said pump; and a processor which causes said first valve to be in said first position and said second valve to be in said second position substantially contemporaneously, and causes said first valve to be in said second position and said second valve to be in said first position substantially contemporaneously.

11. A system for normalized gas detection, which comprises:

a sensor for detection of a selected gaseous species;

a pump for inducing flow of a gas stream to said sensor;

an inlet for a fluid in gas form;

a trap for said gaseous species, said trap being adapted for flow therethough of said fluid in order to remove said gaseous species which may be present therein;

a first valve being variable between a first position in which it affords a path between the sensor and the trap and a second position in which it affords a path between the trap and the pump;

a second valve being variable between a first position in which it affords a path between the sensor and said fluid source and a second position in which it affords a path between the pump and said fluid source;

a first line interconnecting said inlet with said trap;

a second line interconnecting said trap with said first valve;

a third line interconnecting said inlet with said second valve;

a first junction element interconnected with said first valve by a fourth line, with the second valve by a fifth line, and with said sensor by a sixth line;

a second junction element interconnected by a seventh line with said first valve, by an eighth line with said second valve, by a ninth line with said sensor, and by a tenth line with said pump; and a processor that causes said first valve to be in said first position and said second valve to be in said second position substantially contemporaneously, and causes the first valve to be in the second position and said second valve to be in said first position substantially contemporaneously.

12. Apparatus for dispensing alternating fluid feeds in gas form from a fluid source to a detection sensor under the action of a pump to induce the flow of such feeds to the sensor, comprising:

a trap for a select gas species or for one or more unwanted gas species;

a plurality of valve assemblies, each said valve assembly being adapted for interconnection with said detection sensor and with said pump;

said plurality of valve assemblies including a first valve assembly interconnected with said trap, which trap is adapted for interconnection with said fluid source, said first valve assembly being variable between a first position in which it affords a path between the trap and said sensor when interconnected therewith and a second position in which it affords a path between said trap and said pump when interconnected therewith which latter path circumvents the sensor; and said plurality of valve assemblies including a second valve assembly adapted for interconnection with said fluid source, said second valve assembly being variable between a first position in which it affords a path between the sensor and said fluid source when interconnected therewith and a second position in which it affords a path between the pump and said fluid source when interconnected therewith, which latter path circumvents the sensor.

13. The apparatus as defined in claim 12, wherein said trap is one in which a physical mechanism is responsible for removal of said gaseous species which may be present.

14. The apparatus as defined in claim 12, wherein said trap is one in which a chemical mechanism is responsible for removal of said gaseous species which may be present.

15. The apparatus as defined in claim 12, wherein said trap is one in which a combination of physical and chemical mechanisms is responsible for removal of said gaseous species which may be present.

16. The apparatus as defined in claim 12, further comprising a second trap for a second selected gaseous species adapted for interconnection with and interposition between said sensor and said fluid source, said second trap being adapted for flow therethrough of said fluid in order to remove said second gaseous species which may be present therein.

17. Apparatus for dispensing alternating fluid feeds in gas form at substantially constant pressure to a detection sensor, comprising:

an inlet for said fluid in gas form;

a trap for a select gas species that may be present, said trap being interconnected with said inlet, and said trap also being adapted for flow therethough of said fluid in gas form in order to remove said gas species when present;

a first valve in communicating relationship with said trap and adapted for interconnection with said detection sensor, such that when the valve is interconnected with the sensor the valve would be between the trap and the sensor, said first valve also being configured such that, when interconnected with the sensor, in a first position it permits flow of the gas throughput of said trap to said detection sensor and in a second position it diverts flow of said gas throughput to a first shunt line circumventing said detection sensor;

an alternative line interconnected with said inlet and in communicating relationship with a second valve adapted for interconnection with said detection sensor and configured such that, when the valve is interconnected with the sensor, in a first position it permits flow of said fluid from said inlet to said detection sensor and in a second position it diverts flow of said fluid into a second shunt line circumventing said sensor; and a processor which causes said first valve to be in said first position and said second valve to be in said second position substantially contemporaneously, and causes said first valve to be in said second position and said second valve to be in said first position substantially contemporaneously.

18. A method of dispensing alternating fluid feeds in gas form from a fluid source to a detection sensor, which comprises:

inducing fluid in gas form to flow alternately (a) from said fluid source along a first path through a trap for a select gas species that may be present in said fluid in gas form, or for one or more unwanted gas species, such that throughput from the trap comes in contact with said detection sensor, and (b) from said fluid source along a second path circumventing the trap such that said fluid in gas form comes in contact with said detection sensor;

operating a plurality of valve assemblies located variously along said first and second paths such that alternately (i) the throughput of said trap is fed to said detection sensor from said first path while the flow from said second path is diverted around said sensor, and (ii) the flow from said second path is fed to said detection sensor while the throughput of said trap from said first path is diverted around said sensor, whereby the pressure at the detection sensor remains substantially constant;

said plurality of valve assemblies including a first valve assembly interposed along said first path between the trap and the detection sensor, said first valve assembly being variable between a first position in which it affords a path from the trap to the sensor and a second position in which it affords a path that diverts flow from the trap around the sensor; and said plurality of valve assemblies including a second valve assembly interposed along said second path between the fluid source and the detection sensor, said second valve assembly being variable between a first position in which it affords a path from the fluid source to the sensor and a second position in which it affords a path that diverts flow from said fluid source around the detection sensor.

19. The method as defined in claim 18, wherein said trap is one in which a physical mechanism is responsible for removal of said gaseous species which may be present.

20. The method as defined in claim 18, wherein said trap is one in which a chemical mechanism is responsible for removal of said gaseous species which may be present.

21. The method as defined in claim 18, wherein said trap is one in which a combination of physical and chemical mechanisms is responsible for removal of said gaseous species which may be present.

22. A method as defined in claim 18, further comprising the steps of:

measuring a first signal from said detection sensor when the gas throughput from said trap is flowing to said detection sensor; and measuring a second signal from said detection sensor when the fluid from said alternative line is flowing to said detection sensor.

23. The method as defined in claim 18, which further comprises inducing said fluid in gas form to flow to said detection sensor in said first path through a second trap for a second gas species that may be present in said fluid in gas form.

24. The method as defined in claim 23, which further comprises contacting said fluid in gas form from both said second path with a second sensor for detection of said second gaseous species.

25. A method as defined in claim 18, further comprising the step of measuring a pair of signals from said detection sensor, the first signal corresponding to the time of contact of the throughput from said trap with said detection sensor and the second signal corresponding to the time of contact of the throughput from said alternative line is flowing to said detection sensor, the time interval between said measurements being sufficiently abbreviated that the drift effects are mitigated.

26. A method as defined in claim 25, wherein the time interval is predetermined.

27. A method of dispensing alternating fluid feeds in gas form at substantially constant pressure to a detection sensor, which comprises:

inducing fluid in gas form to enter an inlet interconnected (a) with a trap for a gas species that may be present in said fluid in gas form, said trap in turn being interconnected with said detection sensor, and (b) with an alternative line also interconnected with said detection sensor, and causing said fluid in gas form to flow through said trap, and the gas throughput from said trap to flow to said detection sensor, while substantially contemporaneously causing said fluid also to flow through the alternative line and into a shunt line which circumvents the detection sensor, and thereafter causing said fluid in gas form to flow through said alternative line and to said detection sensor while substantially contemporaneously causing said fluid also to flow through the trap, and the gas throughput from said trap to flow into another shunt line which circumvents the detection sensor.

* * * * *